(12) United States Patent
Korb et al.

(10) Patent No.: US 8,187,311 B2
(45) Date of Patent: *May 29, 2012

(54) METHOD AND APPARATUS FOR TREATING GLAND DYSFUNCTION

(75) Inventors: Donald R. Korb, Boston, MA (US); Timothy R. Willis, Raleigh, NC (US); Benjamin T. Gravely, Raleigh, NC (US); Stephen M. Grenon, Durham, NC (US)

(73) Assignee: TearScience, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,990

(22) Filed: Feb. 11, 2011

(65) Prior Publication Data

US 2011/0130729 A1 Jun. 2, 2011

Related U.S. Application Data

(63) Continuation of application No. 11/434,446, filed on May 15, 2006, now abandoned.

(60) Provisional application No. 60/700,233, filed on Jul. 18, 2005.

(51) Int. Cl.
*A61F 9/007* (2006.01)

(52) U.S. Cl. .............. 607/88; 607/89; 606/205; 601/13; 601/15; 604/19; 604/20

(58) Field of Classification Search .................... 607/88, 607/89; 606/205

See application file for complete search history.

(56) References Cited

U.S. PATENT DOCUMENTS

| | | |
|---|---|---|
| 1,006,945 A | 10/1911 | Houston |
| 1,924,315 A | 8/1933 | Hemphill et al. |
| 2,545,724 A | 3/1951 | Curtis |
| 2,891,252 A | 6/1959 | Lazo |
| 3,333,586 A | 8/1967 | Bellis et al. |
| 3,404,678 A | 10/1968 | Von Ardenne |
| 3,667,476 A | 6/1972 | Muller |
| 4,069,084 A | 1/1978 | Mlodozeniec et al. |
| 4,261,364 A | 4/1981 | Haddad et al. |
| 4,387,707 A | 6/1983 | Polikoff |
| 4,778,457 A | 10/1988 | York |
| 4,784,165 A * | 11/1988 | Stein ............................ 132/217 |
| 4,883,454 A | 11/1989 | Hamburg |

(Continued)

FOREIGN PATENT DOCUMENTS

CA 2331257 A1 11/1999

(Continued)

OTHER PUBLICATIONS

Unknown, "TearScience Launches Breakthrough Technology in Canada to Address the Root Cause of Evaporative Dry Eye," Business Wire, Jun. 9, 2011, http://www.businesswire.con/news/home/20110609005860/en/TearScience-Launches-Breakthrough-Technology-Canada-Address-Root, 2 pages.

(Continued)

*Primary Examiner* — David Shay
*Assistant Examiner* — Jeffrey Lipitz
(74) *Attorney, Agent, or Firm* — Withrow & Terranova, PLLC

(57) ABSTRACT

A method and apparatus for treating gland dysfunction caused by gland obstruction in order to restore the natural flow of secretion from the gland comprises the application of a combination of energy, suction, vibration, heat, aspiration, chemical agents and pharmacological agents to loosen and thereafter remove the obstructive material.

40 Claims, 11 Drawing Sheets

U.S. PATENT DOCUMENTS

| | | |
|---|---|---|
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,030,214 A | 7/1991 | Spector |
| 5,151,100 A | 9/1992 | Abele et al. |
| 5,158,082 A | 10/1992 | Jones |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,425,380 A | 6/1995 | Hudson et al. |
| 5,496,311 A | 3/1996 | Abele et al. |
| 5,601,548 A | 2/1997 | Smith et al. |
| 5,643,336 A | 7/1997 | Lopez-Claros |
| 5,700,238 A | 12/1997 | Hyson |
| 5,720,773 A | 2/1998 | Lopez-Claros |
| 5,807,357 A | 9/1998 | Kang |
| 5,836,927 A | 11/1998 | Fried |
| 5,958,912 A | 9/1999 | Sullivan |
| 5,964,723 A | 10/1999 | Augustine |
| 6,024,095 A | 2/2000 | Stanley, III |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,069,084 B2 | 6/2006 | Yee |
| 7,108,694 B2 | 9/2006 | Miura et al. |
| 7,118,591 B2 | 10/2006 | Frank et al. |
| 7,122,013 B2 | 10/2006 | Liu |
| 7,123,968 B1 | 10/2006 | Casscells, III et al. |
| 7,211,070 B2 | 5/2007 | Soroudi |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,594,728 B2 | 9/2009 | Seal et al. |
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| D645,565 S | 9/2011 | Smith et al. |
| 2001/0041886 A1 | 11/2001 | Durkin et al. |
| 2002/0035345 A1 | 3/2002 | Beck |
| 2002/0099094 A1 | 7/2002 | Anderson |
| 2002/0111608 A1* | 8/2002 | Baerveldt et al. ............ 606/6 |
| 2002/0128696 A1 | 9/2002 | Pearl et al. |
| 2002/0156402 A1 | 10/2002 | Woog et al. |
| 2003/0056281 A1* | 3/2003 | Hasegawa ................ 2/428 |
| 2003/0065277 A1* | 4/2003 | Covington ............. 600/573 |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0237969 A1 | 12/2004 | Fuller |
| 2004/0249427 A1 | 12/2004 | Nabilsi |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0220742 A1 | 10/2005 | Breen |
| 2005/0234506 A1* | 10/2005 | Weser ................. 606/205 |
| 2006/0018953 A1 | 1/2006 | Guillon et al. |
| 2006/0030604 A1 | 2/2006 | Elsinger et al. |
| 2006/0055878 A1 | 3/2006 | Yee |
| 2006/0104914 A1 | 5/2006 | Soroudi |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0233859 A1 | 10/2006 | Whitcup et al. |
| 2007/0016256 A1 | 1/2007 | Korb et al. |
| 2007/0049913 A1 | 3/2007 | Grenon et al. |
| 2007/0173799 A1 | 7/2007 | Hsia |
| 2007/0203462 A1 | 8/2007 | Soroudi |
| 2007/0280924 A1 | 12/2007 | Daniels et al. |
| 2008/0051741 A1 | 2/2008 | Grenon et al. |
| 2008/0075787 A1 | 3/2008 | Hibino |
| 2008/0132973 A1 | 6/2008 | Lord et al. |
| 2008/0200848 A1 | 8/2008 | Avni |
| 2009/0043365 A1 | 2/2009 | Friedland et al. |
| 2009/0137533 A1 | 5/2009 | Adkins, Jr. |
| 2009/0306111 A1 | 12/2009 | Nakamura et al. |
| 2010/0100029 A1 | 4/2010 | Maskin |
| 2010/0292630 A1 | 11/2010 | Maskin |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0172302 A1 | 7/2011 | Dalton et al. |
| 2011/0273550 A1 | 11/2011 | Amano et al. |
| 2012/0003296 A1 | 1/2012 | Shantha et al. |
| 2012/0065556 A1 | 3/2012 | Smith et al. |

FOREIGN PATENT DOCUMENTS

| | | |
|---|---|---|
| CA | 2679448 A1 | 9/2008 |
| DE | 202005011496 U1 | 8/2006 |
| EP | 2151438 A1 | 2/2010 |
| EP | 1587468 B1 | 1/2011 |
| JP | 06269473 A | 9/1994 |
| JP | 10085248 A | 4/1998 |
| JP | 11221247 | 8/1999 |
| JP | 2001276113 A | 10/2001 |
| JP | 2002078727 | 3/2002 |
| JP | U3112008 B | 7/2005 |
| JP | 2006198249 | 8/2006 |
| JP | 2010155012 A | 7/2010 |
| WO | 99058131 A1 | 11/1999 |
| WO | 2004041134 A1 | 5/2004 |
| WO | 2006058189 A2 | 6/2006 |

| | | | |
|---|---|---|---|
| WO | 2008024100 A2 | 2/2008 | |
| WO | 2008106228 A2 | 9/2008 | |
| WO | 2009064834 A2 | 5/2009 | |
| WO | 2011085385 A1 | 7/2011 | |

OTHER PUBLICATIONS

Official Action Issued May, 10 2011 for Japanese Patent Application No. 2009-525529.

Partial Translation of Japanese Patent Publication No. 11-221247A.

Partial Translation of Japanese Patent Publication No. 2006-198249A.

Geerling, G., et al., "The international workshop on meibomian gland dysfunction: report of the subcommittee on management and treatment of meibomian gland dysfunction," Mar. 2011, pp. 2050-2064, Investigative Ophthalmology & Visual Science, vol. 52, No. 4.

Korb, Donald R. and Blackie, Caroline A., "Meibomian gland therapeutic expression: Quantifying the applied pressure and the limitation of resulting pain," Eye and Contact Lens, Sep. 2011, pp. 298-301, vol. 37, No. 5, Philadelphia, PA.

Holifield, Karintha and Lazzaro, Douglas R., "Case report: Spontaneous stenotrophomonas maltophilia keratitis in a diabetic patient," Eye and Contact Lens, Sep. 2011, pp. 326-327, vol. 37, No. 5, Philadelphia PA.

Cunniffe, M. Geraldine et al., "Topical antiglaucoma treatment with prostaglandin analogues may precipitate meibomian gland disease," Ophthalmic Plastic and Reconstructive Surgery, Sep.-Oct. 2011, p. 128-129, vol. 27, No. 9, Lippincott Williams and Wilkins, Philadelphia, PA.

Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.

Minco, "Introducing: Thermofoil Heaters," Bulletin HS-202, 9 pages.

Mitra, M. et al., "Tear Film Lipid Layer Thickness and Ocular Comfort after Meibomian Therapy via Latent Heat with a Novel Device in Normal Subjects," Eye, pp. 1-4, 2004.

Mori, A., et al., "Efficacy of the Treatment by the Disposable Eyelid Warming Instrument for Meibomian Gland Dysfunction," Poster Presentation, Hall A, 1 page.

Mori, Asako, et al., "Disposable Eyelid-Warming Device for the Treatment of Meibomian Gland Dysfunction", Japan Journal of Ophthalmology, vol. 47, pp. 578-586, 2003.

Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, pp. 96-99, 2003.

Paugh, J.R. et al., "Meibomian Therapy in Problematic Contact Lens Wear," Entrez PubMed, Optom Vis Sci, vol. 68, No. 11, Nov. 1990, pp. 803-806 (absttract only).

Paugh, Jerry R. et al., "Precorneal Residence Time of Artificial Tears Measured in Dry Eye Subjects," Optometry and Vision Science, vol. 85, No. 8, Aug. 2008, pp. 725-731.

Romero, Juan M., et al., "Conservative Treatment of Meibomian Gland Dysfunction," Contact Lens Association of Ophthalmology, Eye & Contact Lens, vol. 30, pp. 14-19, 2004.

Sullivan, Benjamin D., et al., "Impact of Antiandrogen Treatment on the Fatty Acid Profile of Neutral Lipids in Human Meibomian Gland Secretions," Journal of Clinical Endocrinogy & Metabolism, Vo. 85, No. 12, pp. 4866-4873, 2000.

Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.

Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.

Tobler, David et al., "Nanotech Silver Fights Microbes in Medical Devices," ND & DI, devicelink.com, 1 page.

Toyos, Rolando, "Intense Pulsed Light for Dry Eye Syndrome," Cataract & Refractive Surgery Today, Apr. 2009, pp. 1-3.

Unknown, "Anatomy of the Eye and Orbit," p. 170.

Unknown, "IFU Manual for PNT Model 1000—Rev H," 24 pages.

Vasta, Stephanie, "Aggressive Treatments Developed for Meibomian Gland Dysfunction," Primary Care Optometry News, Nov. 1, 2009, 3 pages.

Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.

Friedland, B., et al., "A novel thermodynamic treatment for meibomian gland dysfunction," Current Eye Research, vol. 36, No. 2, Feb. 2011, pp. 79-87.

Non-Final Rejection mailed Jun. 17, 2009, for U.S. Appl. No. 11/434,446.

Final Rejection mailed Dec. 23, 2009, for U.S. Appl. No. 11/434,446.

Advisory Action mailed Mar. 4, 2010, for U.S. Appl. No. 11/434,446.

Non-Final Rejection mailed Apr. 9, 2010, for U.S. Appl. No. 11/434,446.

Restriction/Election Requirement mailed Oct. 1, 2010, for U.S. Appl. No. 11/434,033.

Non-Final Rejection mailed Jan. 24, 2011, for U.S. Appl. No. 11/434,033.

No Author, "arGentis Licenses Third Treatment for Dry Eye Syndrome", Business Wire, May 12, 2008, accessed Jun. 4, 2008, 2 pages.

No Author, "New Over-the-Counter Dry Eye Drop Now Available to Help Estimated 40 Percent of Americans Who Suffer from Occasional or Chronic Dry Eye", Business Wire News Release, Mar. 21, 2008, accessed Jun. 5, 2008, 4 pages.

Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.

Aronowicz, JD et al. "Short Term Oral Minocycline Treatment of Meibomiantis," Br. J. Ophthalmol, vol. 90, No. 7, Jul. 2006.

Blackie, Caroline A. et al., "Inner Eyelid Surface Temperature as a Function of Warm Compress Methodology," Optometry and Vision Science, vol. 85, No. 8, Aug. 2008, pp. 675-683.

Blackie, Caroline A. et al., "Nonobvious Obstructive Meibomian Gland Dysfunction" Cornea, vol. 29, No. 12, Dec. 2010, pp. 1333-1345.

Blackie, Caroline A. et al., "Recovery Time of an Optimally Secreting Meibomian Gland," Cornea, vol. 28, No. 3, Apr. 2009, pp. 293-297.

Butovich, Igor et al., "Meibomian Lipid Films and the Impact of Temperature," Investigative Opthalmology & Visual Science, vol. 51, No. 11, Nov. 2010, pp. 5508-5518.

Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).

Donnenfeld, Eric et al., "Topical Ophthalmic Cyclosporine: Pharmacology and Clinical Uses," Survey of Ophthalmology, vol. 54, No. 3, May/Jun. 2009, pp. 321-338.

Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.

Foulks, Gary N., "Meibomian Gland Dysfunction: The Past, Present, and Future," Eye and Contact Lens, vol. 36, No. 5, Sep. 2010, pp. 249-253.

Goto, E., et al. "Treatment of Non-Inflamed Obstructive Meibomian Gland Dysfunction by an Infrared Warm Compression Device," Br. J. Ophthalmology, vol. 86, pp. 1403-1407, Dec. 2002.

Goto, Eiki, et al., "Tear Evaporation Dynamics in Normal Subjects and Subjects with Obstructive Meibomian Gland Dysfunction," Investigative Ophthalmology & Visual Science, vol. 44, No. 2, pp. 533-539, Feb. 2003.

Gupta, S. et al. "Docetaxel-Induced Meibomian Duct Inflammation and Blockage Leading to Chalazion Formation," Prostate Cancer Prostatic Diseases, vol. 10, No. 4, 2007.

Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.

Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).

Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).

Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.

Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.

Korb, Donald R. et al., "Increase in Tear Film Lipid Layer Thickness Following Treatment of Meibomian Gland Dysfunction", Lacrimal Gland, Tear Film & Dry Eye Syndromes, Plenum Press, 1994, pp. 293-298.

Korb, Donald R. et al., "Lid Wiper Epitheliopathy and Dry Eye Symptoms," Eye & Contact Lens, vol. 31, No. 1, 2005, pp. 2-8.

Korb, Donald R. et al., "Restoration of Meibomian Gland Functionality with Novel Thermodynamic Treatment Device—A Case Report," Cornea, vol. 29, No. 8, Aug. 2010, pp. 930-933.

Korb, Donald R. et al., "Tear Film Lipid Layer Thickness as a Function of Blinking," Cornea, vol. 13, No. 4, 1994, pp. 354-359.

Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.

Korb, Donald R., O.D., et al., "Meibomian Gland Dysfunction and Contact Lens Intolerance," Journal of the American Optometric Association, vol. 51, No. 3, Mar. 1980, pp. 243-251.

Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.

Kuscu, Naci Kemal, et al., "Tear Function Changes of Postmenopausal Women in Response to Hormone Replacement Therapy," Maturitas, vol. 44, pp. 63-68, 2003.

Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.

Lemp, Michael A., et al., "The Therapeutic Role of Lipids—Managing Ocular Surface Disease," Supplement to Refractive Eyecare of Ophthalmologists, vol. 9, No. 6, Jun. 2005.

Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.

Korb, D et al., "Meibomian gland therapeutic expression: quantifying the applied pressure and the limitation of resulting pain," Eye Contact Lens, vol. 37 No. 5, Sep. 2011, pp. 298-301.

Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutic, vol. 28 No. 1, Feb. 2, 2012, pp. 49-52.

No Author, "TearScience's LipiFlow Multi-center Clinical Study Shows Improved Meibomian Gland Secretions and Dry Eye Symptoms," Business Wire, Mar. 5, 2012, 2 pages.

* cited by examiner

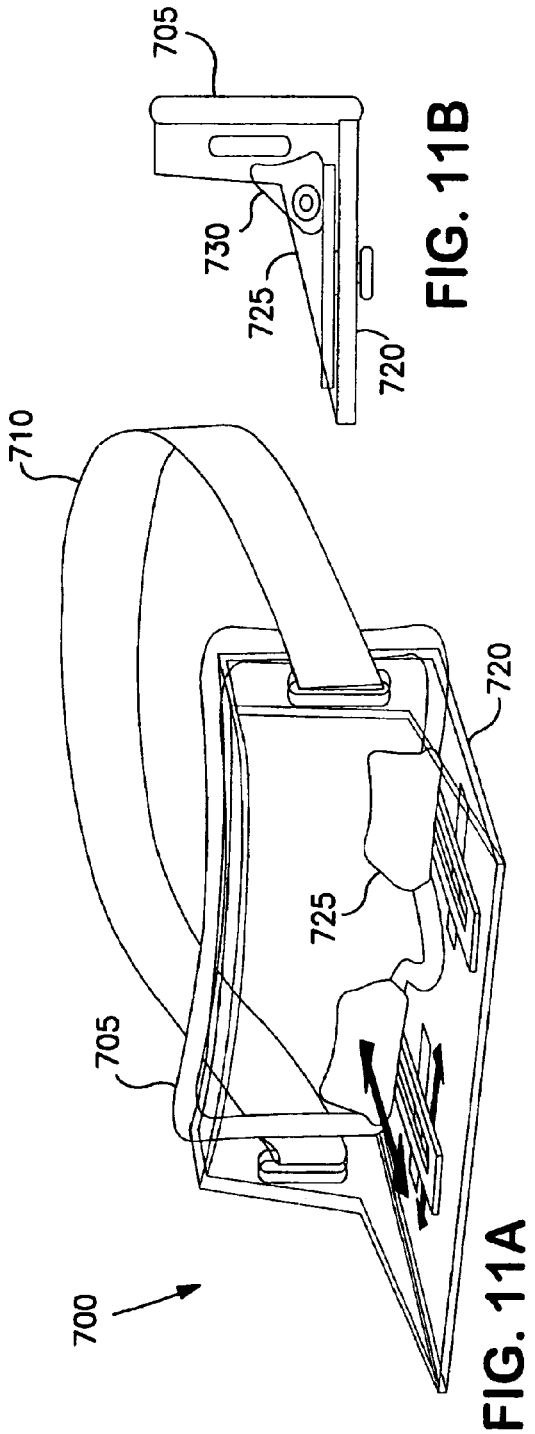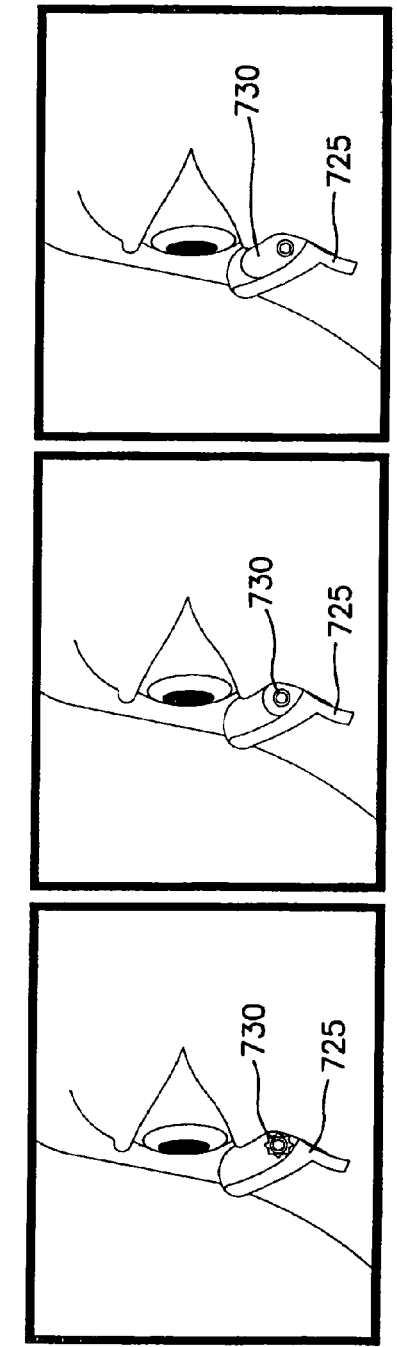

METHOD AND APPARATUS FOR TREATING GLAND DYSFUNCTION

RELATED APPLICATIONS

The present application is a continuation patent application of U.S. patent application Ser. No. 11/434,446, filed May 15, 2006, entitled "METHOD AND APPARATUS FOR TREATING GLAND DYSFUNCTION," which claims priority to U.S. Provisional Patent Application No. 60/700,233, filed Jul. 18, 2005, entitled "METHOD AND APPARATUS FOR TREATING GLAND DYSFUNCTION," both of which are incorporated herein by reference in their entireties.

The present application is also related to U.S. patent application Ser. No. 13/025,951, filed Feb. 11, 2011, entitled "METHOD AND APPARATUS FOR TREATING GLAND DYSFUNCTION," which is incorporated herein by reference in its entirety, and which is also a continuation patent application of U.S. patent application Ser. No. 11/434,446, filed May 15, 2006, entitled "METHOD AND APPARATUS FOR TREATING GLAND DYSFUNCTION."

FIELD OF THE INVENTION

This invention relates generally to the field of treatment of glands in order to restore natural secretory function to obstructed glands within the body and specifically, the meibomian glands of the eye.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common malfunction is the restriction or stoppage of the natural flow of secretions out of the gland. The present invention provides methods and modalities to enhance and/or restore the natural flow of secretions out of the glands.

While the description that follows is directed to the meibomian glands of the eye, it will be understood that the present invention may be employed to treat all of the external glands of the body. With particular reference to the human eye, the tear film covering the ocular surfaces is composed of three layers. The innermost layer in contact with the ocular surface is the mucus layer. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located on both the upper and lower eye lids, with orifices designed to discharge the lipid secretions onto the lid margins, thus forming the lipid layer of the tear film. The typical upper lid has approximately 25 meibomian glands and the lower lid has approximately 20 meibomian glands, which are somewhat larger than those located in the upper lid. The meibomian gland comprises various sac-like acini which discharge the secretion into the duct of the gland. The secretion then passes into the orifices which are surrounded by smooth muscle tissue and the muscle of Riolan which are presumed to aid in the expression of sebum. The meibomian gland orifices open on the lid margin usually along the mucocutaneous junction also known as the gray line. The meibomian gland orifices are assumed to open with blinking and release minute amounts of sebum secretions onto the lid margin and then into the inferior tear meniscus. The lipid "sebum" in the tear meniscus is spread upward and over the tear film of the open eye by the upward blink action. If the lipid secretions are optimal, and adequate lipid layer is maintained at the air interface to minimize evaporation and prevent dry eye states. If the lipid secretions are inadequate the lipid layer is not adequate to minimize evaporation with resulting rapid evaporation leading to dry eye states. Thus, it will be seen that a defective lipid layer or an incorrect quantity or quality of such lipids can result in accelerated evaporation of the aqueous layer which, in turn, causes symptoms which may include symptoms such as dryness, scratching, irritation, burning, tearing, redness, and itchiness, which are collectively be referred to as "dry eye" symptoms.

Dry eye states have many etiologies. A common cause of common dry eye states is the condition known as "meibomian gland dysfunction", a disorder where the glands are obstructed or occluded. As employed herein the terms "occluded" and "obstruction" as they relate to meibomian gland dysfunction are defined as partially or completely blocked or plugged meibomian glands. If completely obstructed the gland cannot secrete. If partially or intermittently occluded the gland may secrete either normal or decreased amounts of sebum. More usually the secretions are altered having semi-solid, thickened, congested secretions, frequently described as inspissated. The secretions may be clear or yellowish, the latter indicating possible infection. meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstruction of the individual meibomian gland orifices and/or the central duct (canal) of the gland which compromises the secretory functions of the individual meibomian glands. More particularly, these keratotic obstructions include a combination of desquamated epithelial cells, keratin, sebaceous ground substance, and bacteria, see, Korb et al., "Meibomian Gland Dysfunction and Contact Lens Intolerance", Journal of the Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction may be limited to subtle alterations of the meibomian gland orifices, subtle or pronounced overgrowth of epithelium over the orifices, and pouting of the orifices of the glands with congealed material acting as the obstructive material under the epithelia overgrowth resulting in the pouting of the orifices.

Hormonal changes include those which occur during menopause, and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, epithelial cells on the eyelid margin tend to grow over the gland orifice thus further restricting sebum flow and exacerbating the dry eye condition.

Additional factors which may cause or exacerbate meibomian gland dysfunction include, age, contact lens wear and hygiene, disorders of blinking, extended computer use, cosmetic use, or other illness, particularly diabetes.

Clinical evaluation of the meibomian glands requires the application of pressure to the external surface of the eyelids over the meibomian glands in order to determine whether secretion is obtained from the individual gland with gentle pressure. If gentle pressure does not provide secretion, forceful expression may be utilized to determine if secretion can be obtained. Thus, the state of an individual meibomian gland can vary from optimal, where clear meibomian sebum is expressed with gentle pressure; to mild or moderate meibomian gland dysfunction where milky fluid or inspissated or creamy secretion may be obtained; to total blockage where no secretion of any sort can be obtained even with the application of extreme pressure (see Korb, et al., "Increase in Tear Film Lipid Layer Thickness Following Treatment of Meibomian Gland Dysfunction", Lacrimal Gland, tear Film, ad Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dye eye".

While the tear film operates as a singular entity and all of the layers thereof are important, the lipid layer, which is secreted from the meibomian glands is of particular significance as it functions to slow the evaporation of the underlying layers and to lubricate the eyelid during blinking which prevents dry eye.

In response to the foregoing, various treatment modalities have been developed in order to treat the dry eye condition, including drops which are intended to replicate and replace the natural tear film, pharmaceuticals which are intended to stimulate the gland and cells providing the components of the tear film and various warm compresses and warming devices which are designed to treat meibomitis and the meibomian glands.

Eye drops such as Refresh®, Soothe® and Systane® are designed to closely replicate the naturally occurring healthy tear film. However, their use and administration is merely a treatment of symptoms and not of the underlying cause. Further, the use of drops is generally for an indefinite length of time and consequently, extended use can become burdensome and costly. Pharmaceutical modalities such as the use of tetracycline have also been suggested to treat meibomian gland dysfunction and one such treatment is disclosed in United States Patent Publication No. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be clinically effective for meibomian gland obstruction, and it may be unnecessary as much meibomian gland dysfunction is the result of an obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover)" to Pflugfelder et al. Again, this proposed treatment appears to treat the symptom of dry eye, as opposed to treatment of the underlying cause and further presents the risks of inducing cataracts and glaucoma. Additionally, the use of topically applied androgens or androgen analogues have also been used to treat acute dry eye signs and symptoms in Keratoconjuctivitis Sicca as disclosed in U.S. Pat. Nos. 5,958,912 and 6,107,289 both titled "Ocular Therapy in Keratoconjunctivitis Sicca Using Topically Applied Androgens of TGF-β" and both issued to Sullivan.

Another modality for the treatment of meibomian gland dysfunction is disclosed in European Patent Application Ser. No. PCT/GB2003/004782 titled "Eyelid Margin Wipes Comprising Chemical Means for Temperature Adjustment". As disclosed in this patent application, an eyelid margin wipe is provided wherein prior to use, a chemical agent is activated that will heat the wipe to about 32° C. to about 55° C. and wherein the temperature will be maintained for at least ten minutes to treat the eyelid margin. This method is not without its drawbacks in that lid irritation can be exacerbated by non-specific heating and the heating range noted as comfortable at over 50° C. would burn the skin. Another method of heating the eyelids and meibomian glands uses near infrared radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., "Treatment of Non-Inflamed Obstructive Meibomian Gland dysfunction by an Infrared Warm Compression Device", British Journal of Ophthalmology, Vol. 86 (2002), pp. 1403-1407.

United States Patent Publication US2004/0237969 titled "Therapeutic Eye and Eye Lid Cover" comprises a pair of goggles that are adapted to deliver humid saturated air around the eyelids. This modality is also discussed in greater detail in the article titled "Tear Film Lipid Layer Thickness and Ocular Comfort after Meibomian Therapy via Latent Heat with a Novel Device in Normal Subjects" by Mitra et al, published in Eye, (2004) at pages 1-4.

United States Patent Publication US2003/0233135 titled "Method and Apparatus for Preventing and Treating Eyelid Problems" by Yee attempts to clear the plugged meibomian glands by means of electrical stimulation of the muscle of Riolan which the invention presumed to aid in the expression of the meibomian gland secretion.

It will be noted that all of the above-noted treatment modalities are not without their inherent drawbacks and deficiencies. For example, the current application of heat to the meibomian glands treatment is very time consuming. Normally, treatment consists of at least fifteen minutes of heat application which is followed by manual expression, which normally consists of placing a cotton swab or firm surface behind the portion of the eye lid where the blocked meibomian gland is located and manually squeezing the obstruction from the gland, the foregoing often being quite painful despite the use of topical anesthesia provided in eye drop form.

It is therefore an object of the present invention to provide a meibomian gland treatment that overcomes the drawbacks and deficiencies of the prior art.

Another object of the present invention is to provide a meibomian gland treatment device that is a single step treatment, thus, eliminating the need for manual expression.

Yet another object of the present invention is to provide a meibomian gland treatment device which treats meibomian gland disease and not merely its symptoms.

Still another object of the present invention is to provide a meibomian gland treatment device that restores the natural sebum flow rather than merely attempting to replace or replicate the naturally occurring tear components.

A still further object of the present invention is to provide a meibomian gland treatment device which minimizes the chance of infection.

A still further object of the present invention is to provide a meibomian gland treatment device that is simple, inexpensive, and easy to use by the health care provider and the patient.

SUMMARY OF THE INVENTION

According to the present invention there is provided a method and apparatus for treating meibomian gland dysfunction wherein the flow of naturally occurring secretions from the meibomian gland is restored. The method comprises applying a regulated force, regulated energy, regulated heat and/or chemical/pharmacological agent or combinations thereof to the eyelid to remove obstruction in order to restore the natural flow of secretion from the meibomian gland. In further aspects of the invention, the obstruction may be dissolved, extracted and/or loosened from the gland wall, softened prior to extraction and/or expansion of the gland orifice or channel such that the normal secretions from the gland are restored. In other aspects of the invention the obstruction may be loosened from the gland wall or softened prior to extraction. Additionally, the force applied to loosen the obstruction may be of a pre-selected magnitude and applied for a pre-selected period of time.

The apparatus comprises means for applying an external or internal force, energy or heat (or a combination of the foregoing) to the gland to loosen the obstruction. Further aspects of the invention include providing means for softening, breaking up, and/or liquefying the obstruction prior to extraction and means for extracting the obstruction.

BRIEF DESCRIPTION OF THE DRAWINGS

FIG. 3b is a broken away side view of the probe tip employed in the embodiment of FIG. 3a.

FIG. 4b is a broken away side view of the probe tip of FIG. 4a.

FIG. 10b is an exploded view of the hand-held probe of the embodiment of FIG. 10a.

FIG. 11a is a perspective view of another embodiment of the meibomian gland treatment apparatus in the form of the hydro-oculator according to the present invention.

FIG. 11b is a side view of the hydro-oculator of FIG. 11a.

FIG. 11c is a schematic side view of the hydro-oculator according to the present invention in place against the lower eyelid.

FIG. 11d is a schematic side view of the hydro-oculator according to the present invention in place against the lower eyelid and showing the fluid filled bladder beginning to expand.

FIG. 11e is a schematic side view of the hydro-oculator according to the present invention in place against the lower eyelid and showing the fluid filled bladder in a further expanded state.

DETAILED DESCRIPTION OF THE PREFERRED EMBODIMENTS

While the present invention will be described more fully hereinafter, it is to be understood at the outset that persons of skill in the art may modify the invention herein described while still achieving the favorable results of this invention. Accordingly, the description that follows is to be understood as a broad teaching disclosure directed to persons of skill in the appropriate arts, and not as limiting upon the present invention.

Figure 1:
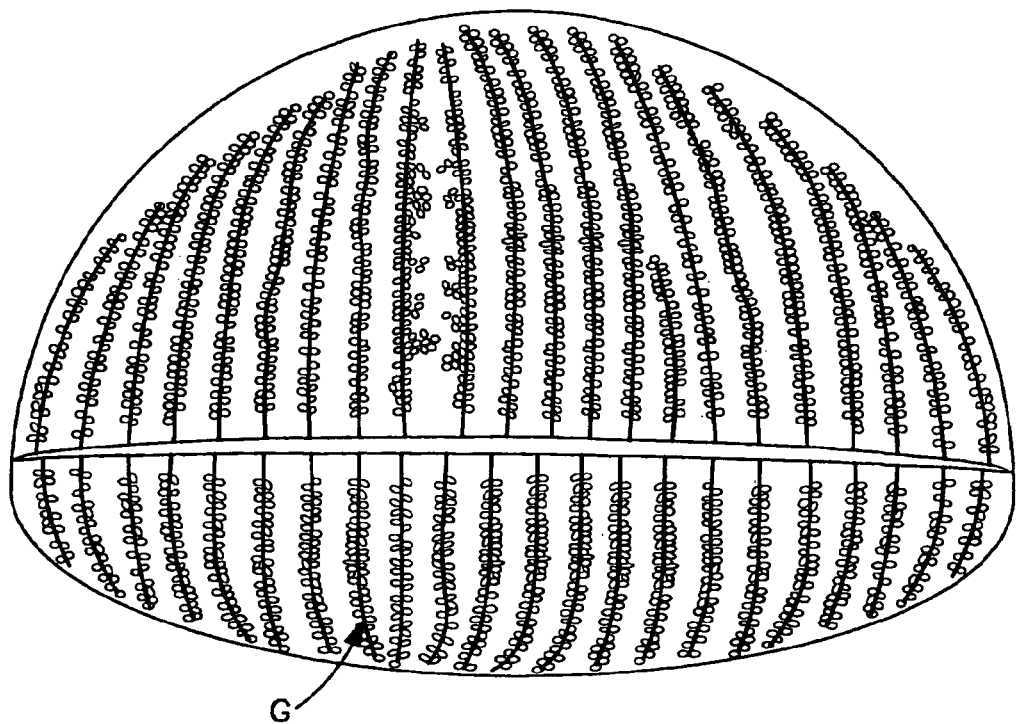
FIG. 1 is a schematic cut away view of the upper and lower eyelids illustrating the meibomian glands in cross section.
Figure 2:
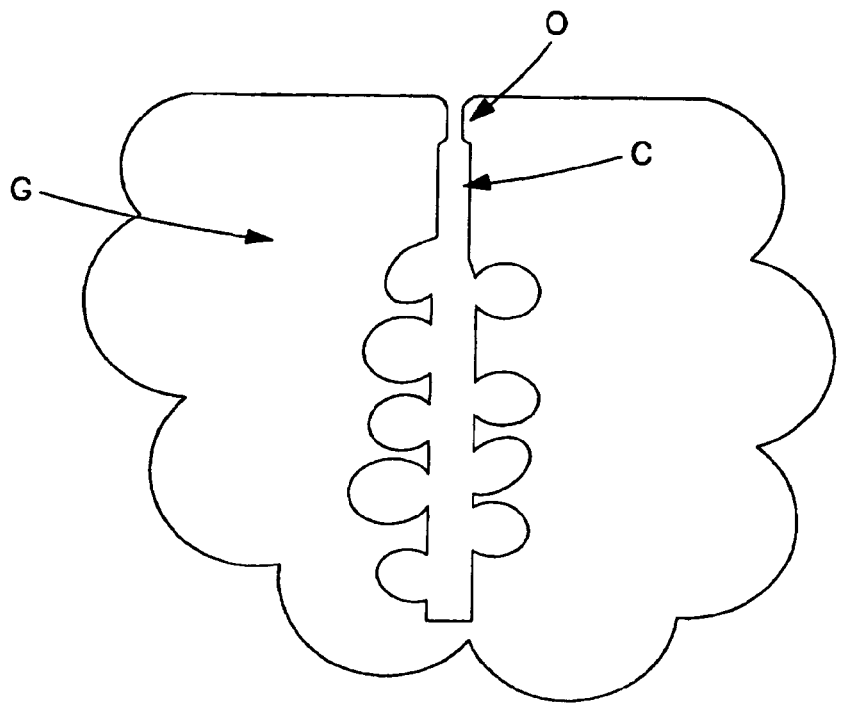
FIG. 2 is a cross sectional view of a single meibomian gland.

Referring now to FIG. 1, the location of the meibomian glands M are shown on the upper and lower eyelids. As briefly stated herein above, the upper lid contains approximately 25 meibomian glands and the lower lid contains approximately 20 meibomian glands. As shown in FIG. 2, each gland includes a channel C into which the secretion flows and an orifice O which opens on to the eyelid margin and through which the secretion must flow in order to be added to the tear film upon blinking. It will be seen that the glands are of different size, depending upon the location in the eyelid and that the orifice O is narrower than the channel C.

As briefly mentioned herein above, obstruction composition will vary with the etiology which produced it. However, the obstruction will, in most cases, consist of a combination of, dead cells, keratin, bacteria, desquamated cells, sebaceous ground substance, milky fluid, inspissated or creamy secretions, or any combination of the foregoing in solid, semi-solid and thickened forms. The obstruction may be in the gland channel, at the gland orifice, atop the gland orifice or a combination of the foregoing. As employed herein, obstruction refers to any of the foregoing.

Thus, it is self-evident that any obstruction of the channel will restrict or prevent secretions from exiting the gland and further, that in order to clear such obstructions or "occlusions", the obstruction may be loosened from the gland wall, and/or broken up, fractured, softened, or liquified so that it will fit through the gland orifice without causing excessive pain. Lastly, the obstruction remnants must be expressed from the gland. The present invention provides a method and apparatus to accomplish these tasks.

According to the method of the present invention, the obstruction P should be softened or liquefied prior to attempting extraction or expression. With respect to the foregoing, the terms "softened" or "liqified" are intended to mean a "non-solid" flowable state. In addition, in order to be clinically satisfactory, softening or liquefying of the obstruction P should be effected as quickly as possible and regulated heat treatment time should be less than five (5) minutes with one to two (1-2) minutes being preferred without causing damage to the surrounding tissues of the ocular globe or the eye, such heat treatments can be electrical, laser heating, hot water conductive heating, infrared heating, ultrasonic. heating, RF heating, etc. This necessarily requires the addition of a greater amount of energy (heating) than is deliverable by the conventional application of hot compresses which according to current practice are applied for 3-15 minutes prior to the clinician attempting to remove the obstruction. Once the obstruction is softened or liquefied, removal is obtained by the application of a regulated force to the gland. More specifically, it is contemplated by the present invention that the force applied be a repeatable controlled force, as more fully explained herein below.

Treatment to remove the obstruction will involve the application of an external regulated force to the eyelid and/or directly over the obstructed orifice to loosen the obstruction within the gland G and the orifice. The means for applying the force may be selected from one or more of a number of modalities wherein the frequency of vibration may be including low frequency vibration (generally less than 1000 Hz), sonic (generally 1000 Hz to 20,000 Hz) or ultrasonic energy (generally greater than 20,000 Hz), fluid jet such as air or water, microwave energy, needles, laser energy, RF energy, aspiration/suction, vacuum, pressure, compression and functional equivalents thereof. In addition, once a modality is chosen, the physician will have to determine the optimum treatment parameters so that each of the foregoing modalities will be applied to the eyelid such that the force (or energy, as appropriate) provided thereby is transmitted through the eyelid tissue to the obstruction. Further, the treatment intensity and length of application of these external forces will vary with the size and composition of the obstruction. Once a treatment protocol is established, the force can either be set per variable within a preselected range. Experiments were performed using an eccentric vibrating motor applied directly to the human eyelids. Bench tests of the vibration revealed the following data points, specifically setting number 3 was shown to be clinically effective to loosen the obstruction within the meibomian gland and orifice:

| Setting | Vibration Freq. (Hz.) | Vibration Amplitude (in/μm) |
| --- | --- | --- |
| 1 | 51 | .001 in. (25.4 μm) |
| 2 | 118 | .004 in. (100 μm) |
| 3 | 165.5 | .0062 in. (157.5 μm) |

Once the obstruction has been loosened from the walls of the gland, it may be operated upon such that it will pass through the orifice O in a manner which causes little or no pain or discomfort to the patent. This can be accomplished by heating to soften or liquefy the obstruction up to a range of thirty seven degrees centigrade (37° C.) to fifty degrees centigrade (50° C.) with the preferred operating range being forty degrees centigrade (40° C.) to forty seven degrees centigrade (47° C.) and desired modality of forty two degrees centigrade (42° C.) to forty six degrees centigrade (46° C.) so that it easily passes through the orifice (or with minimal non-painful expansion thereof). Modalities for heating may include conduction, convection and radiation supplied by one or more of the following: thermal conduction, thermal convection, ultrasonic energy, laser energy, RF energy, direct and/or indirect transfer from heat source and microwave energy which may be applied for a preselected period of time. By varying the amplitude, intensity and length of application, some of the foregoing modalities may also be employed to fracture or break up the obstruction. It will be noted that a closed loop feedback control system, well known to those skilled in the art (not shown) may be employed during heating to measure temperature proximate the eyelid to ensure that the obstruction does, in fact, reach a temperature sufficient to turn the obstructive material into a flowable, liquid or semi-liquid state.

Extraction of the softened, broken apart or fractured obstruction may be accomplished by one or more of the following: needles, micro-needles, aspiration/suction, vacuum, pressure and compression. One embodiment of the invention is a suction system that is placed over the gland orifice may be employed to suck out the components of the softened, loosened or liquefied obstruction or the pieces thereof, as appropriate or alternatively, to employ suction to collect the obstruction as it exits the gland orifice. In order to be clinically effective, the foregoing modalities for extracting or expressing the obstruction should be administered in a fashion that is regulated, i.e., done in a repeatable manner.

Figure 3A:
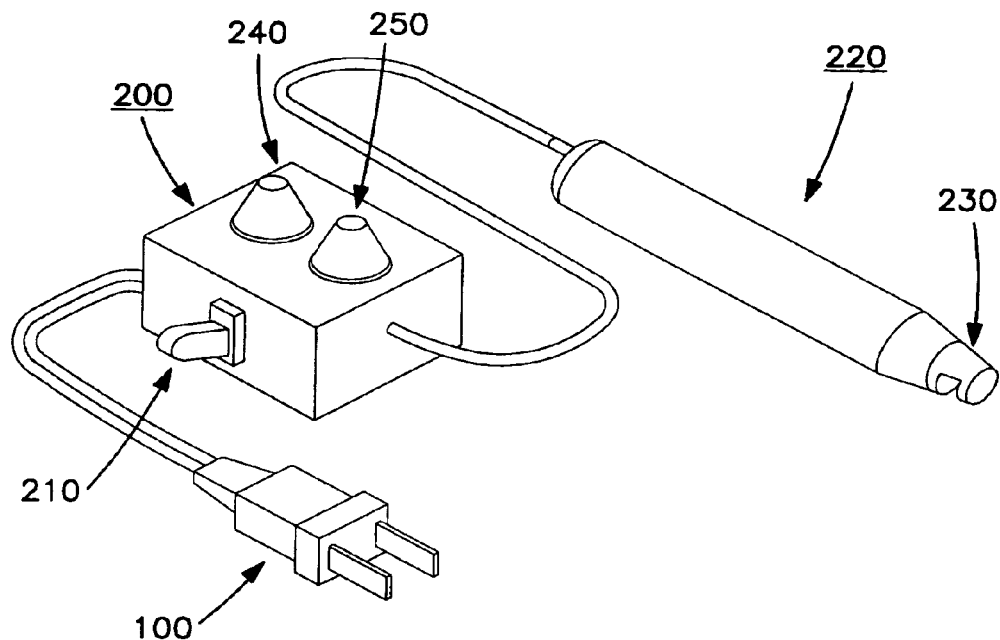
FIG. 3a is a perspective view of a system for clearing obstructed meibomian glands.

An apparatus for unplugging the obstructed gland channel C is schematically illustrated in FIG. 3a. The apparatus comprises a power source 100 which may be direct current (battery powered) or alternating current (wall socket) as desired. The power source 100 is connected to a controller, generally indicated at 200, which includes a power on/power off switch 210. The controller 200 includes a means 220 for applying an external force to the gland to loosen the obstruction. The means 220 includes a probe 230, which is adapted to vibrate at a preselected frequency at preselected amplitude. The probe 230 may vibrate at sonic or ultrasonic frequencies as needed. In addition, means for varying the frequency 240 and amplitude 250 of the probe output, well known to those skilled in the art, are provided. The means 220 for applying the regulated external force or regulated energy to the obstruction may also include fluid jet, air fluid, water fluid, microwave energy, needles, micro-needles, laser energy, RF energy, aspiration, suction, vacuum, pressure, piezoelectric, and compression.

Figure 3B:
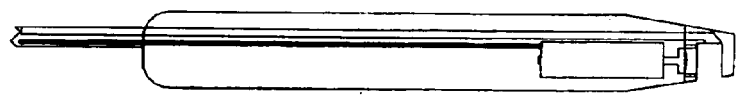
Figure 4A:
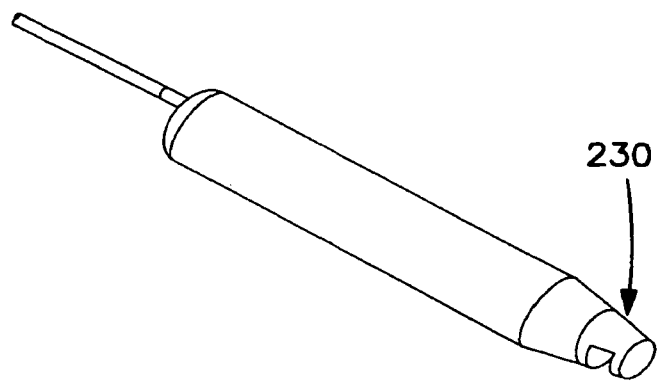
FIG. 4a is a perspective view of a second embodiment of the probe tip according to the present invention.
Figure 4B:
Figure 4C:
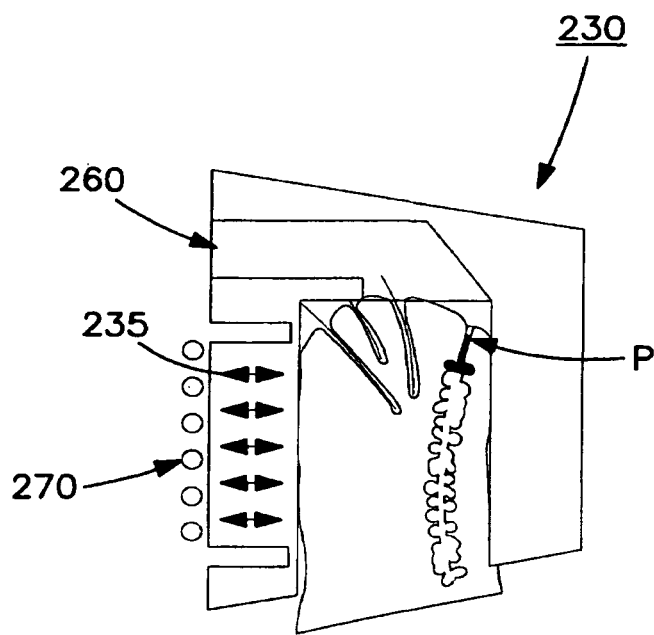
FIG. 4c is a broken away side view of the probe tip of FIGS. 3a and 4a in place on an eye lid.

Turning now to FIG. 3B, a small ultrasonic probe 230 (and specifically the probe tip) is illustrated in FIG. 4C in place on the eyelid. The probe 230 is adapted to deliver ultrasonic vibrational energy through the skin into the obstruction P in order to loosen, liquefy, and/or fracture the obstruction. More specifically, by tuning the probe output so that the obstruction P resonates (by adjusting the frequency and amplitude of the signal) energy is efficiently transferred to the obstruction and sympathetic vibration of the obstruction P occurs with minimal energy transfer to the surrounding tissues. In some instances, vibration alone may be sufficient to change the characteristics of the obstruction P such that vigorous blinking may express the obstruction remnants.

In addition to vibration alternative force, energy, aspiration and/or chemical/pharmacological agents can be used to open up the channel C. The probe may be further equipped with aspiration means 260 (best illustrated in FIG. 4C for introducing aspiration, suction or vacuum into the gland channel C to evacuate the obstruction remnants. Alternatively, heat and aspiration may be employed in lieu of or in addition vibration.

In another aspect of the invention, the probe 230 may be equipped with a means for heating 270 such as a solid state heating element which may be regulated to provide relatively precise amounts of energy in the previously mentioned ranges that assists in softening, liquifying or melting the obstruction P via heat transfer through the tissue when the probe is placed against the tissue.

Figure 5:
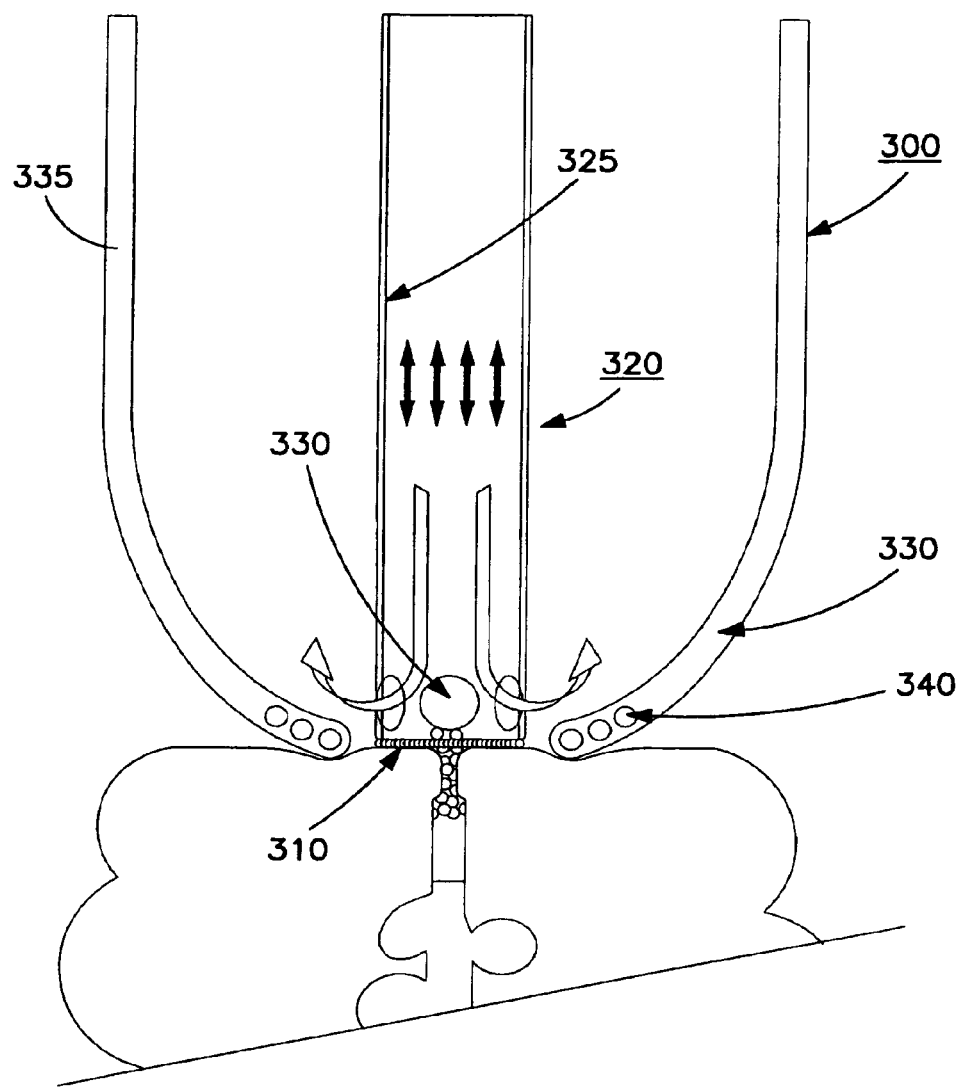
FIG. 5 is broken away side view of an alternate for clearing obstructed meibomian glands according to the present invention.

A second embodiment of the invention (FIG. 5) employs microdermabraision or exfoliation to remove any cells or cellular material that may have overgrown the gland opening. Microdermabraision is a process that was developed for use in dermatology to remove dead skin cells. As shown in FIG. 5 a probe or tip 330 is equipped with an abrasive surface 310 that is adapted to scrape the skin. The abrasive employed is usually a diamond power or other suitable material, well known to those skilled in the art. An inner tube 320 having a central bore 325 includes holes defining openings 330 through which a fluid such as air is pumped. An outer covering 335 surrounds the tube 320, but at its lower edge extends slightly lower and is spaced from the abrasive surface 310 and a space is defined between the lower ends of the respective tubes 320, 335. The outer covering is connected to aspiration, vacuum, and/or suction that operates as described herein below.

In operation, the clinician would place the abrasive tip 310 in contact over the gland orifice creating a seal between the tip and the skin. Movement of the probe 330 would cause the abrasive 310 on the bottom of the tip to separate the cells from the skin and the aspiration, suction or vacuum would extract the cellular material from the vicinity of the gland opening. In addition, depending upon the obstruction, aspiration, suction and/or vacuum alone may be sufficient to extract the obstruction.

Additional features may also be providing to the microdermabraision tip such as a heating element 340 which could be placed in the outer covering 335 near the tip. In addition, the inner tube 320 could be equipped such that ultrasonic energy could be delivered to the obstruction as discussed herein above.

Another embodiment of the invention may employ a chemical agent to clean the gland margin and to remove or exfoliate cells from the meibomian gland orifice. For example Ophthaine® or a similar pharmacological agent may be employed to assist in removing epithelial cells from over the gland orifice. A probe similar to that shown in FIG. 5 may be employed, except that the inner tube will deliver the chemical agent and the suction applied by the outer covering will be used to evacuate the used chemical agent and cellular material mixture away from the gland margin. Similarly, the heating and vibrational features discussed above may also be included.

A further embodiment of the invention may deliver vibrational and/or thermal energy to the obstruction P without contacting the gland. One potential energy source is laser light supplied by titanium, argon, krypton or microwave energy. Extraction of the obstruction would be accomplished by the means described herein above.

Figure 6A:
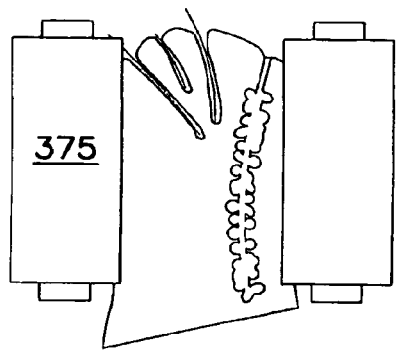
FIG. 6a is a side view of an alternate embodiment of the probe tip having rollers for clearing obstructed meibomian glands according to the present invention.
Figure 6B:
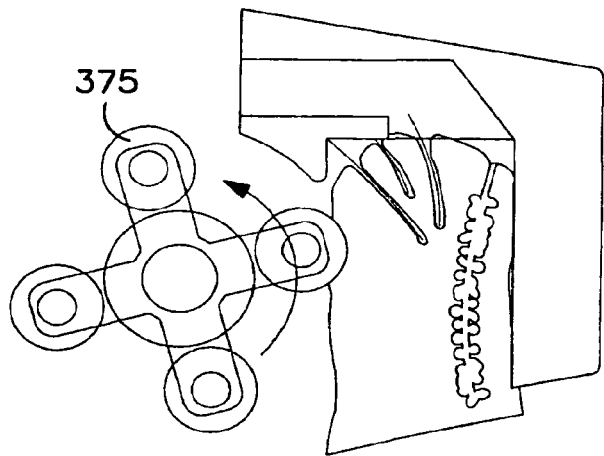
FIG. 6b is a side view of another alternate embodiment of the probe tip having rollers for clearing obstructed meibomian glands according to the present invention.
Figure 7:
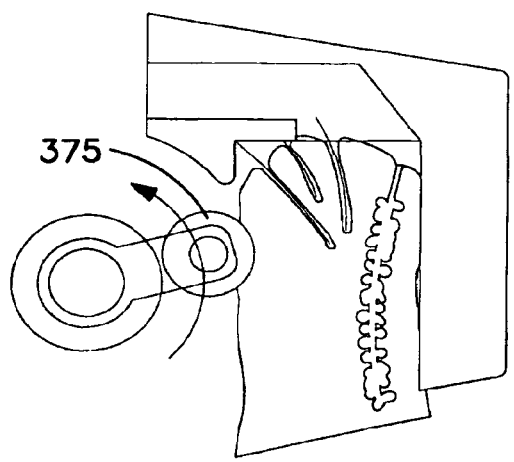
FIG. 7 is a side view of another alternate embodiment of the probe tip having rollers for clearing obstructed meibomian glands according to the present invention.

A third embodiment of the invention employs pressure applied to the tissue as shown in FIGS. 6a, 6b and 7 by rollers (or drums) 375 which are placed in front of and/or behind the meibomian gland with the rollers applying constant regulated pressure to the meibomian glands to apply a "milking" type force to expel the obstruction to return the gland to normal secretion levels. The rollers can be connected to heat, aspiration, vacuum, and/or suction that operate as described herein.

In operation, the physician would place the rollers 375 in contact with the eyelid, either inside, outside or both. Lateral movement of the rollers 375 would cause pressure to be applied to the gland to remove the obstruction. Alternatively, aspiration, suction and/or vacuum could be applied to extract the obstruction and material from the vicinity of the gland opening. In addition, depending upon the obstruction, aspiration, suction and/or vacuum alone may be sufficient to extract the obstruction.

Additional features may also be provided to the rollers such as a regulated heating element (not shown) which could be placed in the outer covering near the tip as shown in FIG. 6A. In addition, the roller 375 could be equipped such that ultrasonic energy could be delivered to the obstruction as discussed herein above.

Figure 8:
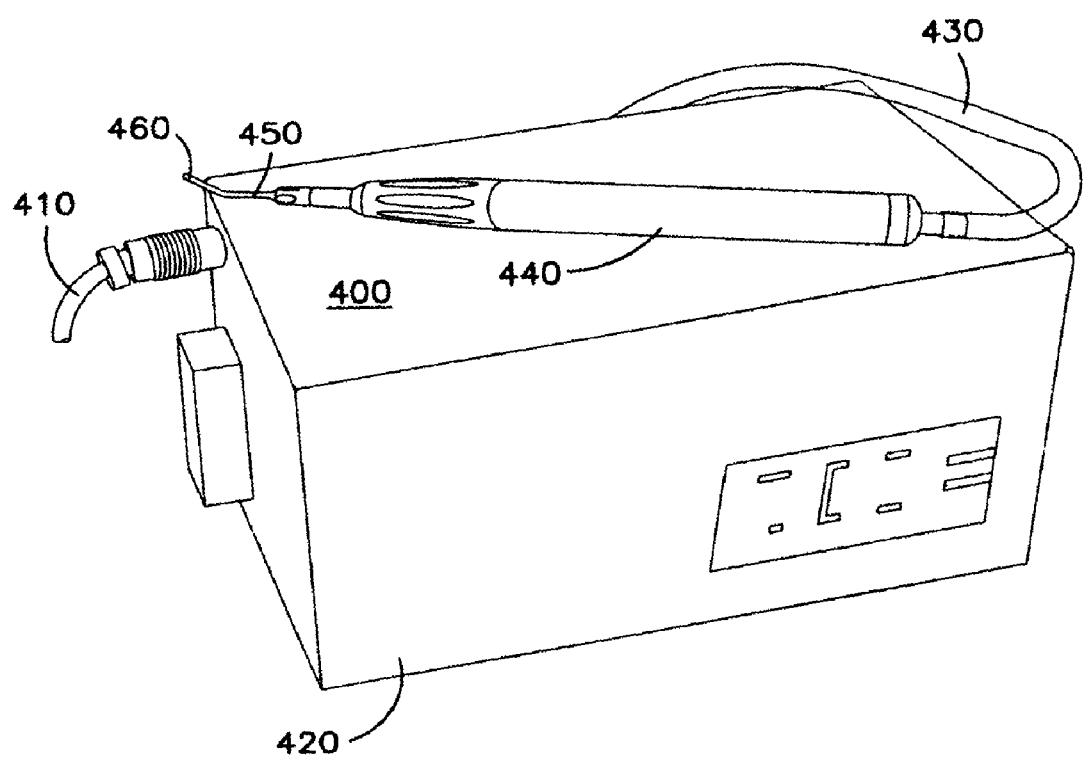
FIG. 8 is a perspective view of a suction device for clearing glands according to the present invention.

FIG. 8 illustrates a prototype hand held suction system generally indicated at 400 that was constructed. The system comprised an AC power supply 410 which powered a suction pump 420 to which tubing 430 was connected. At the opposite end of tubing 430 a probe 440 was connected. A tip 450 having a 1 mm diameter and a 200 micron orifice was attached to the end of the probe 440. The probe end 460 was curved for ergonomic access to the gland orifice. In use, the tip 450 is placed on or proximate the gland orifice and the applied vacuum is used to collect the obstruction as it exits the orifice or may alternatively be employed to assist in expression of the obstruction.

Figure 9:
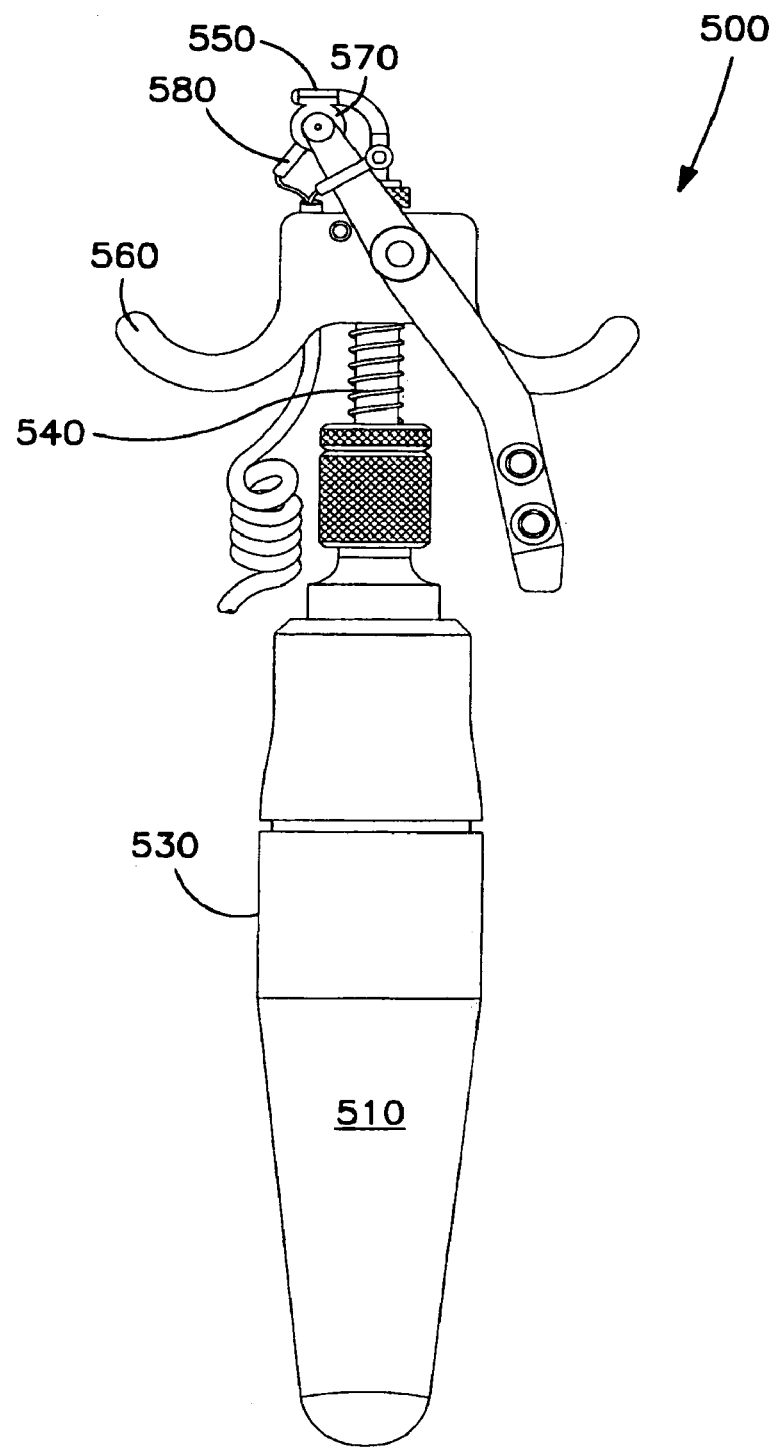
FIG. 9 is a side view of another embodiment of the apparatus for clearing meibomian glands according to the present invention.

FIG. 9 illustrates another prototype of a hand held apparatus generally indicated at 500 that was constructed. The system comprised a power supply 510 which powered an electromagnet (not shown) which was encased in a handle 530 that may be easily held by the clinician in one hand. A rod 540 is mounted for reciprocating motion to the output of the electromagnet. The throw or amount of movement of the rod 540 is 0.5 mm. At the end of rod 540 is mounted a back plate 550 which is substantially perpendicular to the axis of rod 540. Further, a lever 560 is pivotally mounted to rod 540 and operates to actuate a roller 570. A heating means or heater 580 was mounted in backplate 550. The heater 580 was also provided with an appropriate power source. In operation, the device is positioned such that the back plate 550 is positioned between the cornea and the back surface of the eye lid. The lever 560 is actuated such that the roller 570 comes into contact with the front surface of the eye lid. The arc of the roller is such that the eye lid is squeezed between the foregoing. The clinician may elect to maintain the back plate and the roller under tension for a preselected period of time to soften the obstruction. Once the desired temperature has been reached, further pressure on the lever 560 will cause the roller to move from the bottom of the meibomian gland (the end away from the orifice) to the top of the gland to express the obstruction from the gland in a "milking type" motion. Thus, a repeatable regulated method for opening obstructed meibomian glands is provided.

Figure 10A:
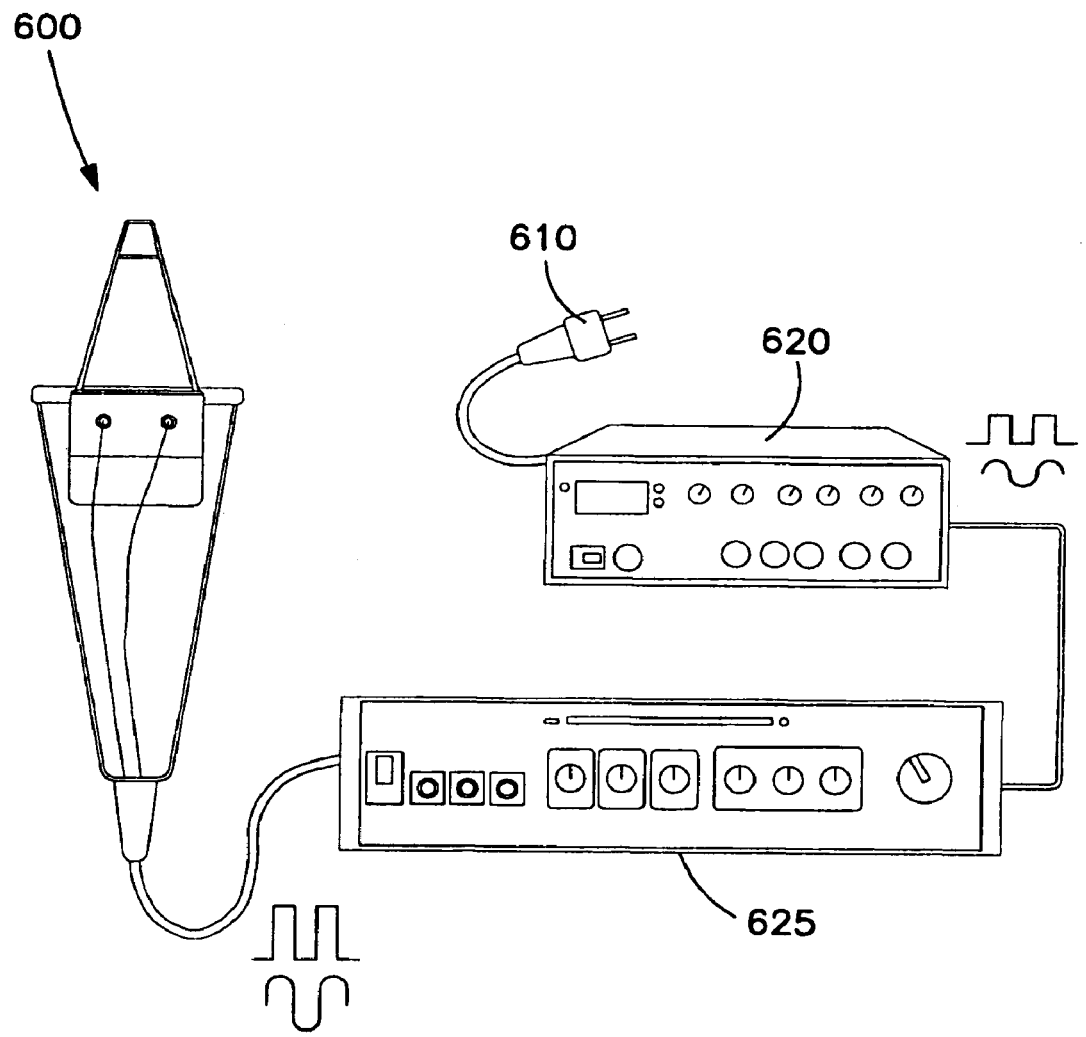
FIG. 10a is a schematic view of another embodiment of the apparatus for clearing meibomian glands according to the present invention.
Figure 10B:
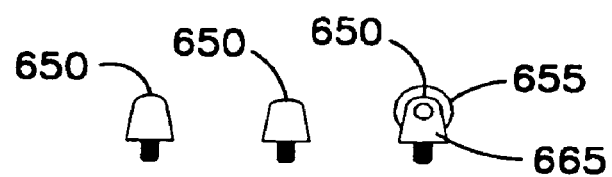
Figure 10B:
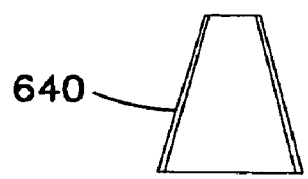
Figure 10B:
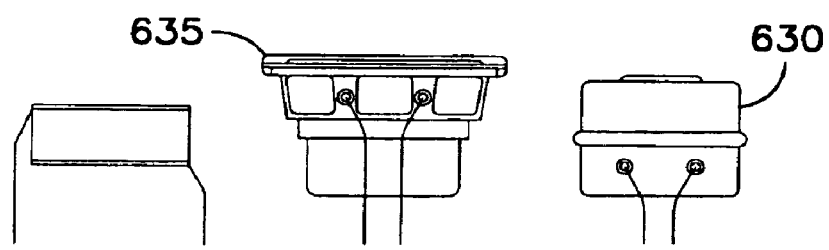
Figure 10B:
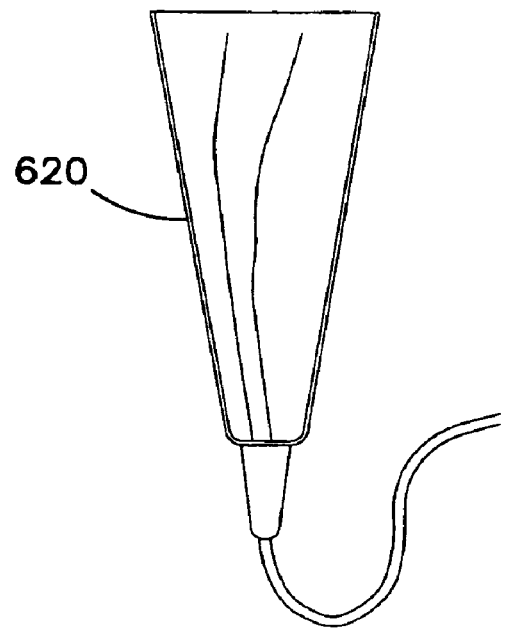
Figure 10C:
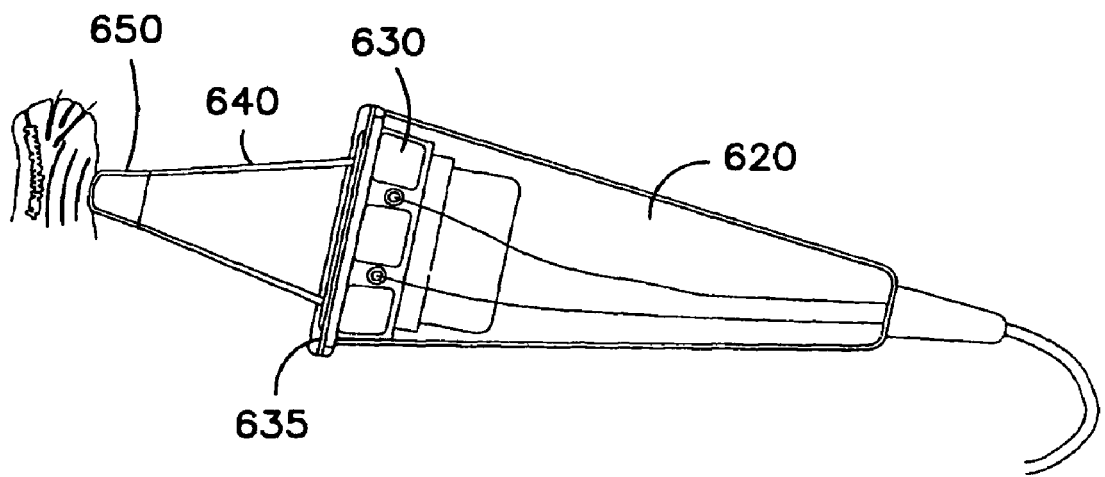
FIG. 10c is a side view of the hand-held probe of FIGS. 10a and 10b applying force to an eyelid.

The embodiment illustrated in FIGS. 10A through 10C, the present invention prototype is a hand held apparatus generally indicated at 600. The apparatus comprises a power source 610 which may be a DC source such as a battery or an AC source similar to those discussed herein above. The power source 610 resides within a housing 620. The power source 610 provides electrical current to a wave form generator 625 which powers an acoustic amplifier 630 (for example, a small audio speaker) also located within housing 620 and mounted at an ergonomic angle therein. The acoustic amplifier 630 is programmed to vibrate in a wave format at a frequency of 0 to 200 Hz at an amplitude in the range of 0.1 mm to 5 mm, 0.25 mm to 5 mm, or 0.5 mm to 5 mm. Initial experiments indicate that free air amplitude of 3-4 mm at a frequency of 60 Hz to 125 Hz is well tolerated and after 10-30 seconds of application seems to impart a natural numbing effect to the eyelid/gland. Mounted in operative association atop the acoustic amplifier 630 is an annulus 635 that floats thereon and includes a cone shaped housing 640 extending perpendicularly away from the amplifier 625 that encloses the amplifier 625. The end of the housing 640 is adapted to mount a variety of tips 650. For example, the tip may comprise a roller 655 mounted for rotation in a cradle 665. Further, the tip 650 may be modified to include a regulated heating element (not shown) that acts to soften the obstruction. Other tip configurations may include a vacuum for collecting the obstruction after expression thereof from the gland and different tip configurations to apply various contact areas and resulting forces. Thus, it will be seen that the obstruction is actually subjected to a pair of forces, the first being the weight of the device itself on the gland which may be combined with additional pressure by the health care provider pressing on the gland plus the additional intermittent force delivered to the gland by the vibratory or pulsatory force of the tip 650. The first force may be a fixed constantly applied force or one that increases to a preselected maximum. Testing has indicated that use of the foregoing method, i.e., applying a first force to the meibomian gland and a second pulsatile force to the meibomian gland allows delivery of a greater quantity of energy to the obstruction while lowering the perceived pain level to the patient. It is believed that this is the result of an overall lower degree of localized nerve stimulation about the orbit. Heating the gland is also beneficial in the event softening of the obstruction is needed prior to expression thereof.

Another embodiment of the invention is shown in FIGS. 11A through 11E wherein the treatment apparatus is incorporated into a goggle-like device, termed herein as the "hydro-oculator" which is a head borne device that locates the treatment mechanism proximate the eyelids, generally indicated at 700. The hydro-oculator 700 comprises a flexible frame 705 having a headband 710 (which may be elastic) connected thereto at each end. Connected to the bottom of the frame 705 is a molded housing 720 which has an angled leg 725 which is adapted to overlie the cheek bone when the apparatus is in use. Further, an expandable fluid or gas impermeable container referred to herein as a bladder 730 is positioned within the cavity defined by the space between the housing and the lower eye lid. A pumping mechanism is provided that facilitates movement of a fluid or gas, collectively referred to herein as a "medium" (not shown) into and out of each of the respective bladders 730. According to the invention, the patient would position the hydro-oculator 700 on his or her head such that the leg 725 of molded housing 730 rests on the upper cheek bone as best shown in FIGS. 11C through 11E. The regulated heated medium is pumped into the bladders 730 causing partial expansion thereof in order to apply a pressure to the eyelids in the range of from zero to fifty pounds per square inch (50 psi). The bladder containing the heated medium (a water based solution being preferred) is positioned on the eyelids over the meibomian glands for a preselected period of time (up to thirty minutes) to soften the obstruction. It is desirable to place the heat source in direct contact with the eyelids which thereby transmits thermal energy to the meibomian glands, in contrast to the prior art which heats a confined space in front of the open eye where heat could be transmitted to the ocular bulbi structures such as the crystalline lens which introduces the possibility of cataract formation. Thereafter, the bladder is slowly expanded to a preselected maximum such that the force on the gland increases from the bottom up to the top or orifice end of the gland such that the obstruction is expressed therefrom in a "milking" type of action. Milking may be applied at a preselected frequency between zero and five hertz (0-5 Hz) and for a preselected period of time, usually not more than thirty minutes. In addition, the medium may be "pulsed", i.e., milkingly moved into and out of the bladder to further facilitate expression of the obstruction from the gland. Pulsing may also be achieved by providing an external force to the bladder and transmitting the force through the fluid into the gland. Pulsing may be applied at a preselected frequency between zero and one hundred hertz (0-100 Hz) for a preselected period time, usually not more than thirty (30) minutes. A chemical or pharmacological agent may be inserted into the meibomian gland to assist in softening the obstruction and any of the extraction modalities mentioned above may be further employed to assist in removing the obstruction.

Another embodiment of the invention may employ a chemical agent or compound to clean the glandular margin to remove or exfoliate cells from the gland orifice. A probe similar to that shown in FIG. 5 may be employed, except that the outer drum or roller will deliver the chemical agent and the suction applied by the outer covering will be used to evacuate the used chemical agent and cellular material mixture away from the gland margin. Similarly, the heating and vibrational features discussed above may also be included.

A further embodiment of the invention may deliver vibrational and/or thermal energy to the obstruction P without contacting the gland. One potential energy source is laser light supplied by a titanium-sapphire, argon, krypton, RF energy or microwave energy. Extraction of the obstruction would be accomplished by the means described herein above.

Another embodiment of the invention employs the use of chemical or pharmacological agents to open or dilate the gland and gland orifice wherein the obstruction naturally is expressed and returns the normal secretions of the gland. Alternatively, the chemical or pharmaceutical agent would be used to soften or breakup the obstruction with such obstruction being expressed with the use of devices as defined above or combinations thereof. Chemical or pharmacological agents may also be used in connection with the device for post treatment. Once the glands have been opened then chemical or pharmacological agents may be used to enhance the normal production or secretion to maintain the glands in its unblocked state.

Dilation of the meibomian gland channel and orifice may also be employed to loosen or free the obstruction from the gland walls. Dilation may be accomplished by chemical, pharmacological, or mechanical means.

Stimulation of the meibomian gland may also be employed in conjunction with the other modalities discussed above to loosen or fracture the obstruction.

As mentioned herein above, the present invention has been described in detail on conjunction with the figures in connection with the meibomian glands of the eye. The reader will note that the principals of this invention may be applied with equal efficacy to the other glands of the human body and potentially to valuable domesticated farm animals to treat various ailments.

What is claimed is:

1. An apparatus for treating meibomian gland dysfunction wherein the flow of naturally occurring secretion from a meibomian gland in an eyelid may be occluded due to the presence of an obstruction within a meibomian gland channel of the meibomian gland, comprising:

a probe comprising a thermal energy applicator, at least one roller, a back plate, and an opening disposed between the at least one roller and the back plate, wherein the at least one roller is configured to be controllably actuated to regulate the distance between the at least one roller and the back plate;

wherein the opening in the probe is configured to receive at least a portion of an eyelid such that the at least one roller is disposed adjacent to a first surface of the eyelid and the back plate is disposed adjacent to a second surface of the eyelid opposite the first surface of the eyelid;

wherein the thermal energy applicator is disposed in the probe and configured to apply thermal energy to the meibomian gland channel; and wherein the at least one roller is configured to be controllably actuated to regulate the distance between the at least one roller and the back plate such that the at least one roller comes into contact with the eyelid and applies a regulated force to the eyelid disposed in the opening to squeeze the meibomian gland channel in the eyelid between the at least one roller and the back plate to express the obstruction from within the meibomian gland channel through a meibomian gland orifice of the meibomian gland.

2. The apparatus of claim 1, further comprising a controller electrically coupled to the probe and configured to actuate the at least one roller to regulate the distance between the at least one roller and the back plate.

3. The apparatus of claim 1, wherein the probe further comprises a lever configured to be actuated to actuate the at least one roller.

4. The apparatus of claim 3, wherein the at least one roller is disposed on an end of the lever.

5. The apparatus of claim 3, wherein the back plate is disposed on an end of a rod provided in the probe.

6. The apparatus of claim 5, wherein the lever is pivotally mounted to the rod.

7. The apparatus of claim 1, wherein the at least one roller is configured to be actuated such that the at least one roller comes into contact with the eyelid and squeezes the meibomian gland channel in a direction from a bottom of the meibomian gland channel to a top of the meibomian gland channel.

8. The apparatus of claim 1, wherein the at least one roller is configured to be actuated such that the at least one roller comes into contact with the eyelid and applies a regulated constant force to the meibomian gland channel.

9. The apparatus of claim 1, wherein the at least one roller is configured to be actuated such that the at least one roller comes into contact with the eyelid and applies a regulated milking force to the meibomian gland channel.

10. The apparatus of claim 1, wherein the at least one roller further comprises a vibration means configured to apply a regulated pulsatile force to the meibomian gland channel.

11. The apparatus of claim 10, wherein the regulated pulsatile force is applied at a preselected frequency.

12. The apparatus of claim 11, wherein the preselected frequency is less than 1000 Hz.

13. The apparatus of claim 11, wherein the preselected frequency is between about 50 Hz and about 500 Hz.

14. The apparatus of claim 11, wherein the preselected frequency is between about 60 Hz and about 300 Hz.

15. The apparatus of claim 10, wherein the regulated pulsatile force has an amplitude of between 0.1 mm and 5.0 mm.

16. The apparatus of claim 10, wherein the regulated pulsatile force has an amplitude of between about 0.5 mm and 1.5 mm.

17. The apparatus of claim 10, wherein the regulated pulsatile force has an amplitude of approximately 1.00 mm.

18. The apparatus of claim 1, wherein the probe applies a second force to the meibomian gland channel to extract the obstruction from within the meibomian gland channel and through the meibomian gland orifice.

19. The apparatus of claim 18, wherein the second force is comprised of a pulsatile force.

20. The apparatus of claim 18, wherein the regulated force is comprised of a regulated constant force, and the second force is comprised of a pulsatile force.

21. The apparatus of claim 1, wherein the thermal energy applicator is comprised of a heater, wherein the heater is configured to apply thermal energy to the meibomian gland channel during squeezing of the eyelid to soften the obstruction within the meibomian gland channel.

22. The apparatus of claim 21, wherein the heater is comprised of a heating element.

23. The apparatus of claim 21, wherein the heater is comprised of a solid-state heating element.

24. The apparatus of claim 21, wherein the heater is configured to apply a regulated thermal energy to the meibomian gland channel.

25. The apparatus of claim 21, wherein the heater is configured to apply conduction thermal energy to the meibomian gland channel.

26. The apparatus of claim 21, wherein the heater is configured to apply convention thermal energy to the meibomian gland channel.

27. The apparatus of claim 21, wherein the heater is configured to apply radiation thermal energy to the meibomian gland channel.

28. The apparatus of claim 21, wherein the heater is configured to apply infrared thermal energy to the meibomian gland channel.

29. The apparatus of claim 21, wherein the heater is configured to apply ultrasonic thermal energy to the meibomian gland channel.

30. The apparatus of claim 21, wherein the heater is configured to apply laser thermal energy to the meibomian gland channel.

31. The apparatus of claim 21, wherein the heater is configured to apply radio frequency (RF) thermal energy to the meibomian gland channel.

32. The apparatus of claim 21, wherein the heater softens the obstruction from a meibomian gland wall within the meibomian gland channel through the application of the thermal energy to the meibomian gland channel.

33. The apparatus of claim 21, wherein the heater applies sufficient thermal energy to the meibomian gland channel to loosen the obstruction within the meibomian gland channel.

34. The apparatus of claim 21, wherein the heater applies sufficient thermal energy to the meibomian gland channel to liquefy the obstruction within the meibomian gland channel.

35. The apparatus of claim 21, wherein the heater applies applies sufficient thermal to the meibomian gland channel to partially liquefy the obstruction within the meibomian gland channel.

36. The apparatus of claim 1, further comprising an aspirator disposed in the probe and configured to be disposed proximate the meibomian gland orifice during application of the regulated force to the front surface of the eyelid to soften the obstruction within the meibomian gland channel, to assist in extracting the obstruction from the meibomian gland channel.

37. The apparatus of claim 1, further comprising a tube disposed in the probe and configured to deliver a chemical agent or chemical compound into the meibomian gland channel.

38. The apparatus of claim 1, wherein one of the at least one roller is configured to be positioned in front of the meibomian gland.

39. The apparatus of claim 1, wherein one of the at least one roller is configured to be positioned behind the meibomian gland.

40. The apparatus of claim 1, wherein a first one of the at least one roller is configured to be positioned in front of the meibomian gland and a second one of the at least one roller is configured to be positioned behind the meibomian gland.

* * * * *

UNITED STATES PATENT AND TRADEMARK OFFICE
CERTIFICATE OF CORRECTION

PATENT NO. : 8,187,311 B2  Page 1 of 1
APPLICATION NO. : 13/025990
DATED : May 29, 2012
INVENTOR(S) : Donald R. Korb et al.

It is certified that error appears in the above-identified patent and that said Letters Patent is hereby corrected as shown below:

Claim 35, column 14, lines 37-38, change "applies applies" to --applies--.

Signed and Sealed this
Seventh Day of August, 2012

David J. Kappos
*Director of the United States Patent and Trademark Office*